US009044393B2

(12) United States Patent
Sebillotte-Arnaud et al.

(10) Patent No.: US 9,044,393 B2
(45) Date of Patent: *Jun. 2, 2015

(54) OIL-RICH O/W EMULSION

(75) Inventors: Laurence Sebillotte-Arnaud, L'Hay les Roses (FR); Dominique Bordeaux, Longpoint sur Orge (FR)

(73) Assignee: L'OREAL, Paris (FR)

( * ) Notice: Subject to any disclaimer, the term of this patent is extended or adjusted under 35 U.S.C. 154(b) by 1260 days.

This patent is subject to a terminal disclaimer.

(21) Appl. No.: 11/154,602

(22) Filed: Jun. 17, 2005

(65) Prior Publication Data

US 2006/0013787 A1 Jan. 19, 2006

Related U.S. Application Data

(60) Provisional application No. 60/590,923, filed on Jul. 26, 2004.

(30) Foreign Application Priority Data

Jul. 16, 2004 (FR) ...................................... 04 51546

(51) Int. Cl.
| | |
|---|---|
| A61K 8/02 | (2006.01) |
| A61K 8/25 | (2006.01) |
| A61K 8/39 | (2006.01) |
| A61K 8/88 | (2006.01) |
| A61Q 19/00 | (2006.01) |
| A61K 8/06 | (2006.01) |
| A61Q 1/14 | (2006.01) |
| A61Q 1/00 | (2006.01) |
| A61Q 5/00 | (2006.01) |

(52) U.S. Cl.
CPC . *A61K 8/062* (2013.01); *A61Q 1/00* (2013.01); *A61Q 19/001* (2013.01); *A61K 8/0204* (2013.01); *A61K 8/06* (2013.01); *A61K 8/25* (2013.01); *A61K 8/39* (2013.01); *A61K 8/88* (2013.01); *A61Q 1/14* (2013.01); *A61Q 5/00* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 4,606,913 A | 8/1986 | Aronson et al. | |
| 4,746,460 A * | 5/1988 | Taylor | 516/76 |
| 5,756,110 A * | 5/1998 | Allard et al. | 424/401 |
| 6,333,362 B1 | 12/2001 | Lorant | |
| 6,511,655 B1 * | 1/2003 | Muller et al. | 424/59 |
| 6,927,241 B2 * | 8/2005 | Ansmann et al. | 516/77 |
| 2002/0031534 A1 | 3/2002 | Horino | |
| 2003/0073689 A1 | 4/2003 | Senee | |
| 2005/0089541 A1 * | 4/2005 | Lacoutiere | 424/401 |
| 2005/0106196 A1 | 5/2005 | Cassin et al. | |
| 2005/0118216 A1 | 6/2005 | Senee | |
| 2005/0118285 A1 | 6/2005 | Lacoutiere | |

FOREIGN PATENT DOCUMENTS

| | | |
|---|---|---|
| EP | 0 268 164 | 5/1988 |
| JP | 07-173380 | 7/1995 |
| JP | 2001-179076 | 7/2001 |
| WO | WO 98/09721 | 3/1998 |
| WO | WO 01/89678 | 11/2001 |

OTHER PUBLICATIONS

Balsam et al (ed.s), "Cosmetics Science and Technology", Second Edition, vol. 3, pp. 583-597 (1974).*
Database CA Chemical Abstracts Service, Columbus, Ohio, US: AN: 137:52043, S. Baba: "Oily Cosmetic Compositions Having Improved Storage Stability and Preservability," XP002270586 & JP-A-2002279525 (Kao Corp.), (2002).

* cited by examiner

*Primary Examiner* — Bethany Barham
*Assistant Examiner* — Barbara Frazier
(74) *Attorney, Agent, or Firm* — Oblon, McClelland, Maier & Neustadt, L.L.P.

(57) ABSTRACT

The present invention relates to a composition for topical application in the form of an oil-in-water emulsion, wherein it contains:
  a lipophilic phase (A)
  an emulsifying system (B)
  an aqueous phase (C),
  one or more fillers having an oil uptake greater than or equal to 75 ml/100 g,
  the emulsifying system (B)/lipophilic phase (A) weight ratio ranging from 0.04 to 0.2.
This composition is preferably obtained according to the phase inversion (PIT) emulsification technique and it can in particular constitute a cosmetic or dermatological composition.

20 Claims, No Drawings

OIL-RICH O/W EMULSION

REFERENCE TO PRIOR APPLICATIONS

This application claims priority to U.S. provisional application 60/590,923 filed Jul. 26, 2004, and to French patent application 0451546 filed Jul. 16, 2004, both incorporated herein by reference.

FIELD OF THE INVENTION

The present invention relates to a composition in the form of an oil-in-water emulsion that is rich in oil and can be obtained by phase inversion, and to uses thereof in particular in the cosmetics or dermatological field, in particular for the treatment of keratin materials, for making up the skin and for removing makeup from the skin, the mucous membranes and/or the eyelashes. Preferably, the invention composition is for topical use, in particular cosmetic and/or dermatological use.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

It is known practice, in the cosmetics or dermatological field, to use oily compositions, i.e. compositions comprising only oils or containing very little water, for example as products for removing makeup from the skin, as massage products for caring for the face, the body, the scalp or the feet, as a conditioner balm, as an antisun oil or else as a care oil for the shower. These compositions have the advantage of being effective since the oils are directly in contact with the skin, but they have the drawback of being too liquid, and therefore not very practical for use since they run during application. In addition, they have the drawback of lacking a freshness and of leaving a greasy effect when they are applied to the skin.

The oil-in-water (O/W) emulsions consist of an oily phase (or lipophilic phase) dispersed in an aqueous phase. They therefore have an external aqueous phase and are therefore products that are more pleasant to use because of the feeling of freshness that they provide. However, they have the drawback of relatively lacking effectiveness, in particular for removing makeup or any other application where the greater the amount of oil present, the greater the effectiveness, since the oily phase or lipophilic phase that contains the oils and that constitutes the internal phase is not directly available and, as a result, the oil is less effective since the amount of oil is less. Now, for example for cleansing the face, and more especially for removing makeup, which consists in removing all makeup products, women seek to obtain as effective a makeup removal as possible.

In order to ally effectiveness and cosmetic attractiveness, it is advantageous to produce an oil-in-water (O/W) emulsion containing a large amount of oil and, in order to facilitate handling, it is advantageous for the emulsion to be in the form of a cream, which makes it possible to use it directly by taking it up with the fingers without involving a support such as cotton wool, and without fear that the product will run.

The production of O/W emulsions with a high oil concentration is often difficult, and the emulsions obtained are often unstable. These emulsions are conventionally obtained mechanically, for example by emulsification with a stator rotor or using a high-pressure homogenizer, because a great deal of mechanical energy is required to divide the dispersed phase up into small drops. In order to stabilize these emulsions, emulsifying surfactants of the oil-in-water type, i.e. with an HLB (HLB=hydrophilic lipophilic balance) ranging from 8 to 18 are generally added thereto, which emulsifiers, due to their amphiphilic structure, go to the oily phase/aqueous phase interface and thus stabilize the dispersed oil droplets. Despite the presence of the emulsifiers, the emulsions can have a tendency to destabilize (coalescence and then separation of the aqueous and oily phases with release of oil). To improve the stability of these emulsions, the concentrations of emulsifiers can be increased; however, a high concentration of emulsifiers can result in a rough, clingy or sticky feel, and also in problems of innocuousness with respect to the skin, the eyes and the scalp.

To resolve the problems of stability of conventional O/W emulsions, it has been proposed to prepare O/W emulsions obtained by the phase inversion temperature technique (PIT emulsions), in which the average size of the globules constituting the oily phase is within given limits, namely between 0.1 and 4 μm (100 to 4000 nm). The principle of phase inversion temperature (or PIT) emulsification is, in theoretical terms, well known to those skilled in the art; it was described in 1968 by K. Shinoda (J. Chem. Soc. Jpn., 1968, 89, 435). It was shown that this emulsification technique makes it possible to obtain stable fine emulsions (K. Shinoda and H. Saito, J. Colloïd Interface Sci., 1969, 30, 258). This technology was applied in cosmetics as early as 1972 by Mitsui et al. ("Application of the phase-inversion-temperature method to the emulsification of cosmetics"; T. Mitsui, Y. Machida and F. Harusawa, American. Cosmet. Perfum., 1972, 87, 33).

The principle of this technique is as follows: a mixture of an aqueous phase and an oily phase is prepared and is brought to a temperature greater than the PIT temperature, the phase inversion temperature of the system, i.e. the temperature at which the equilibrium between the hydrophilic and lipophilic properties of the emulsifier(s) used is attained; at higher temperature, i.e. greater than the phase inversion temperature (>PIT), the emulsion is of water-in-oil type and, as it cools, this emulsion inverts at the phase inversion temperature so as to become an emulsion of oil-in-water type, having beforehand passed through a state of microemulsion. This process makes it possible to readily obtain emulsions with a diameter generally less than 4 μm.

Document WO-A-01/89678 describes oil-rich emulsions having a ratio by weight of oily phase to aqueous phase of 0.7. However, the rate of release of the oil from these emulsions is not sufficient to obtain good effectiveness, as shown in the comparative examples given below.

SUMMARY OF THE INVENTION

There remains a need to improve the rate of release of the oil from fine O/W emulsions, in order to obtain better effectiveness, and therefore to have O/W emulsions that, although they contain a large amount of oils, are stable while at the same time having an improved rate of release of the oil.

The inventors have found, surprisingly, that the addition of certain mineral and organic solid particles makes it possible to accelerate the oil release rate and to improve the effectiveness of the compositions.

DETAILED DESCRIPTION OF THE PREFERRED EMBODIMENTS

One subject of the present invention is a composition in the form of an oil-in-water emulsion, wherein it comprises:
- a lipophilic phase (A) present in an amount of at least 60% by weight relative to the total weight of the composition,
- an emulsifying system (B) present in an amount of 2 to 20% by weight relative to the total weight of the composition and comprising at least one emulsifier having an HLB ranging from 8 to 18,
- from 0.5 to 10% by weight, relative to the total weight of the composition, of one or more fillers having an oil uptake greater than or equal to 75 ml/100 g,
- an aqueous phase (C) present in an amount of less than or equal to 30% by weight relative to the total weight of the composition,
- the emulsifying system (B)/lipophilic phase (A) weight ratio ranging from 0.04 to 0.2.

Because it is preferably intended for topical application, the composition of the invention preferably contains a physiologically acceptable medium. The term "physiologically acceptable medium" is intended to mean a medium suitable for topical application to the skin or the integuments, i.e. compatible with the skin, the mucous membranes, the lips, the eyelashes, the eyes, the hair and the nails. This composition can in particular constitute a cosmetic or dermatological composition.

In the present application, the term "lipophilic phase" is intended to mean the phase containing the lipophilic compounds, namely, in particular oils (lipophilic constituents that are liquid at ambient temperature), gums, pastes and waxes. They are, for example, triglycerides, hydrocarbons, esters, ethers, silicones, as described below, and any of the lipophilic additives optionally present. The emulsifiers and co-emulsifiers of the emulsifying system are not part of the lipophilic phase as defined above.

It is important to have a sufficient amount of lipophilic phase and in particular of oils so as to obtain a creamy texture, and a problem that forms part of the basis of the invention was the difficulty in obtaining a composition having a creamy texture with small-sized globules, that contains sufficient oils while at the same time nevertheless being very stable.

In the present application, the term "fillers" is intended to mean solid particles that may be mineral or organic. The oil uptake, characteristic of these solid particles used in the composition according to the invention, is determined according to AFNOR standard NF T30-022 (May 1972), as explained in detail hereinafter.

The O/W emulsions according to the invention can be obtained by means of phase inversion temperature technology and are characterized by preferred features including:
- their viscosity: they are mainly creams,
- their appearance, that can range from opaque to translucent,
- the pH, that ranges from 3 to 8,
- the small size of the droplets of the oily phase,
- their high oil release rate (or breaking rate) as will be demonstrated hereinafter,
- when they are rinsed off, good re-emulsification of the oil during rinsing with water so as to limit the lipophilic residue on the skin or the hair.

In addition, these emulsions are pleasant to use because of the external aqueous phase and they thus ally effectiveness and cosmetic attractiveness.

The compositions can be used in different ways according to the desired applications: they can, for example, be wiped or rinsed off with water for a sun product, or else wiped or rinsed off with a tonic for a makeup-removing product, or alternatively rinsed off with water for a haircare product after shampooing.

The compositions according to the invention may be in the form of more or less thick creams that are opaque to translucent, and they may or may not be able to flow under their own weight according to their viscosity. The viscosity measured at 25° C. with the Rheomat 180 measuring device at 200 rpm (revolutions per minute) should preferably be greater than or equal to 1 Pa·s. The Rheomat 180 is equipped with a different rotor according to the viscosities, for example with a rotor 3 for the range of viscosities from 0.2 to 4 Pa·s, and with a rotor 4 for the range of viscosities greater than 2 Pa·s. When measured under the conditions indicated above, the viscosity of the compositions of the invention can range, for example, from 1 to 30 Pa·s, and preferably from 1 to 20 Pa·s. This viscosity is generally measured 10 minutes after the rotation of the rotor has begun.

When the viscosity is measured by means of a Haake RS 150 device, determined by $0.1\ s^{-1}$ flow measurements, it can range from 500 to 5000 Pa.

The mean size of the droplets of oily phase is measured by light diffraction using a Mastersizer 2000 particle sizer (sold by Malvern Instruments). These measurements are carried out on the emulsion diluted in a solution of SDS (sodium dodecyl sulphate) at 1% in water. A computer program makes it possible to obtain the mean diameter by volume D[4.3] (µm) (see operators guide, Malvern Instruments, December 1998, p. 61 to 67).

The mean size D[4.3] (µm) of the droplets of oily phase of the composition of the invention prefereably ranges from 0.09 µm to 4 µm, more particularly from 0.1 µm to 2 µm, and most preferably from 0.1 µm to 1 µm.

Emulsifying System

The emulsifying system (B) used in the composition according to the invention preferably comprises one or more emulsifiers whose solubility in the oil increases with the increase in temperature, which emulsifiers make it possible to obtain emulsions by phase temperature inversion. The HLB (hydrophilic lipophilic balance) of these emulsifiers ranges from 8 to 18, and preferably from 10 to 16. They may be chosen in particular from ethoxylated fatty alcohols, ethoxylated fatty acids, partial glycerides of ethoxylated fatty acids, polyglycerolated fatty acid triglycerides and ethoxylated derivatives thereof, and mixtures thereof.

The emulsifiers are preferably chosen from ethoxylated fatty alcohols or ethoxylated fatty acids having the formulae (I) and (II) below:

$$R-O-(CH_2-CH_2-O)_mH \quad (I)$$

$$R-COO-(CH_2-CH_2-O)_mH \quad (II)$$

where R is a saturated or unsaturated, linear or branched hydrocarbon-based chain having from 10 to 24 carbon atoms, and m is an integer ranging from 8 to 50.

As ethoxylated fatty alcohols, mention may, for example, be made of the addition products of ethylene oxide with lauryl alcohol, in particular those containing from 9 to 50 oxyethylenated groups (having CTFA names Laureth-9 to Laureth-50); the addition products of ethylene oxide with behenyl alcohol, in particular those containing from 9 to 50 oxyethylenated groups (having CTFA names Beheneth-9 to Beheneth-50); the addition products of ethylene oxide with cetearyl alcohol (mixture of cetyl alcohol and of stearyl alcohol) in particular those containing from 9 to 30 oxyethylenated groups (having CTFA names Ceteareth-9 to Ceteareth-30; the addition products of ethylene oxide with cetyl alcohol, in particular those containing from 9 to 30 oxyethylenated groups (having CTFA names Ceteth-9 to Ceteth-30); the addition products of ethylene oxide with stearyl alcohol, in particular those containing from 9 to 30 oxyethylenated groups (having CTFA names Steareth-9 to Steareth-30; the addition products of ethylene oxide with isostearyl alcohol, in particular those containing from 9 to 50 oxyethylenated groups (having CTFA names Isosteareth-9 to Isosteareth-50); and mixtures thereof.

As ethoxylated fatty acids, mention may, for example; be made of the addition products of ethylene oxide with lauric acid, palmitic acid, stearic acid or behenic acid, and mixtures thereof, in particular those containing from 9 to 50 oxyethylenated groups, such as laurates of PEG-9 to PEG-50 (having CTFA names: PEG-9 laurate to PEG-50 laurate); palmitates of PEG-9 to PEG-50 (having CTFA names: PEG-9 palmitate to PEG-50 palmitate); stearates of PEG-9 to PEG-50 (having CTFA names: PEG-9 stearate to PEG-50 stearate); palmitostearates of PEG-9 to PEG-50; behenates of PEG-9 to PEG-50 (having CTFA names: PEG-9 behenate to PEG-50 behenate); and mixtures thereof.

Mixtures of these oxyethylenated derivatives of fatty alcohols and of fatty acids can also be used.

Preferably, the emulsifying system of the composition of the invention contains, as emulsifier, at least one ethoxylated fatty alcohol, and more particularly behenth-10.

The emulsifying system may also contain one or more co-emulsifiers. As co-emulsifiers, mention may, for example, be made of fatty alcohols having 8 to 30 carbon atoms, for instance cetyl alcohol, stearyl alcohol or behenyl alcohol; fatty acids having 8 to 30 carbon atoms, for instance palmitic acid, stearic acid or behenic acid; fatty esters of glycerol, for instance glyceryl stearate; oxyethylenated derivatives of these fatty alcohols, fatty acids and fatty esters of glycerol, containing 2 to 8 ethylene oxide groups, and mixtures thereof.

The emulsifying system is present in an amount ranging from 2 to 20%, preferably from 3 to 16%, and better still from 3 to 11%, by weight relative to the total weight of the composition.

The emulsifying system (B)/lipophilic phase (A) weight ratio ranges from 0.04 to 0.2, preferably from 0.06 to 0.18. As indicated above, the term "lipophilic phase" is intended to mean all the constituents that are not hydrophilic and that are different from the emulsifiers or co-emulsifiers of the emulsifying system.

Lipophilic Phase

The lipophilic phase, also called oily or fatty phase, comprises lipophilic constituents, i.e. oils and other lipophilic substances present in the composition, and also any lipophilic additives optionally present. The lipophilic phase contains at least one oil, in particular a cosmetic oil.

The term "oil" is intended to mean a fatty substance that is liquid at ambient temperature (25° C.).

The lipophilic phase is present in an amount of at least 60% by weight relative to the total weight of the composition. The amount of lipophilic phase can range, for example, from 60 to 80% by weight, preferably from 61 to 75% by weight, and better still from 62 to 70% by weight, relative to the total weight of the composition. The lipophilic phase may comprise only oils (liquid fatty substances) or it may comprise a mixture of oils and of other fatty substances. However, the amount of oils is preferably at least 50% by weight relative to the total weight of the composition, and preferably at least 60% relative to the total weight of the composition.

Included as oils that can more particularly be used for the composition of the invention, mention may, for example, be made of:

hydrocarbon-based oils of animal origin, such as perhydrosqualene (or squalane);

synthetic esters and ethers, in particular of fatty acids, such as oils of formulae $R^1COOR^2$ and $R^1OR^2$ in which $R^1$ represents the residue of a fatty acid containing from 8 to 29 carbon atoms, and $R^2$ represents a branched or unbranched hydrocarbon-based chain containing from 3 to 30 carbon atoms, for instance Purcellin oil, isononyl isononanoate, isopropyl myristate, 2-ethylhexyl palmitate, 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate, fatty alcohol heptanoates, octanoates and decanoates; polyol esters, such as propylene glycol dioctanoate, neopentyl glycol diheptanoate and diethylene glycol diisononanoate; pentaerythrityl esters such as pentaerythrityl tetraisostearate; lipophilic derivatives of amino acids, such as isopropyl lauroyl sarcosinate (INCI name: Isopropyl Lauroyl sarcosinate) sold under the name Eldew SL 205 by the company Ajinomoto;

linear or branched hydrocarbons of mineral or synthetic origin, such as mineral oils (mixture of petroleum-derived hydrocarbon-based oils; INCI name: Mineral oil), volatile or non-volatile paraffin oils, and derivatives thereof, petroleum jelly, polydecenes, isohexadecane, isododecane, hydrogenated isoparaffin such as Parleam® oil sold by the company NOF Corporation (INCI name: Hydrogenated Polyisobutene);

volatile or non-volatile silicone oils, such as volatile or non-volatile polymethylsiloxanes (PDMS) containing a linear or cyclic silicone chain, that are liquid or pasty at ambient temperature, in particular cyclopolydimethylsiloxanes (cyclomethicones) such as cyclopentasiloxane and cyclohexadimethylsiloxane; polydimethylsiloxanes containing alkyl, alkoxy or phenyl groups that are pendent or at the end of the silicone chain, which groups have from 2 to 24 carbon atoms; phenyl silicones such as phenyl trimethicones, phenyl dimethicones, phenyltrimethylsiloxydiphenylsiloxanes, diphenyl dimethicones, diphenylmethyl-diphenyltrisiloxanes, 2-phenylethyltrimethyl siloxysilicates, and polymethylphenylsiloxanes;

fluoro oils such as those that are partially hydrocarbon-based and/or silicone based, for instance those described in document JP-A-2-295912;

ethers such as dicaprylic ether (CTFA name: Dicaprylyl ether) and $C_{12}$-$C_{15}$ fatty alcohol benzoates (Finsolv TN from Finetex);

and mixtures thereof.

Other lipophilic constituents that may be present in the oily phase include, for example, plant oils, waxes; gums such as silicone gums (dimethiconol); silicone resins such as trifluoromethyl($C_1$-$C_4$)alkyl dimethicone and trifluoropropyl dimethicone; and mixtures thereof.

When the composition of the invention is used as a makeup-removing composition, it preferably contains at least one makeup-removing oil, to which one or more other oils, that may or may not be makeup-removing, may be added.

The makeup-removing oils can be chosen in particular from the branched hydrocarbons of mineral or synthetic origin described above, fatty esters and mixtures thereof.

The fatty esters are preferably those obtained from an alcohol comprising a linear or branched chain, having from 1 to 17 carbon atoms, and from a fatty acid comprising a linear or branched chain, having from 3 to 18, and preferably from 12 to 17, carbon atoms.

Included as fatty esters that can be used as makeup-removing oils, mention may more particularly be made of butyl myristate, butyl laurate, butyl stearate, isopropyl stearate, isostearyl isostearate, 2-ethylhexyl palmitate (or octyl palmitate), 2-ethylhexyl pelargonate (or octyl pelargonate), 2-ethylhexyl stearate (or octyl stearate), 2-octyldodecyl myristate, 2-ethylhexyl hydroxystearate (or octyl hydroxystearate), isopropyl laurate, isopropyl myristate, isopropyl palmitate, isobutyl palmitate, isobutyl stearate, isocetyl stearate, diisopropyl adipate, 2-diethylhexyl adipate (or dioctyl adipate), diisocetyl adipate, 2-ethylhexyl succinate (or octyl succinate), diisopropyl sebacate, 2-ethylhexyl malate (or octyl malate), pentaerythrityl caprate/caprylate, pentaerythrityl tetraisostearate, 2-ethylhexyl hexanoate (or octyl hexanoate), ethyl laurate, methyl myristate, octyldodecyl octanoate, isodecyl neopentanoate, isostearyl neopentanoate, cetearyl isononanoate, isodecyl isononanoate, isononyl isononanoate, isotridecyl isononanoate, lauryl lactate, myristyl lactate, cetyl lactate, ethyl myristate, myristyl propionate, 2-ethylhexyl 2-ethyl hexanoate (or octyl 2-ethyl hexanoate), 2-ethylhexyl octanoate (or octyl octanoate), 2-ethylhexyl caprate/caprylate (or octyl caprate/caprylate), 2-ethylhexyl monococoate (or octyl monococoate), methyl palmitate, isobutyl myristate, ethyl palmitate, isohexyl laurate, hexyl laurate, isopropyl isostearate, and mixtures thereof.

According to a particular embodiment of the invention, when the composition according to the invention constitutes a makeup-removing composition, it contains one or more fatty esters chosen from those mentioned above.

As branched hydrocarbons of mineral or synthetic origin that can be used in the composition according to the invention constituting a makeup-removing composition, mention may in particular be made of isoparaffin, isohexadecane, isododecane, and hydrogenated polyisobutene such as Parleam® oil.

Aqueous Phase

The composition according to the invention comprises an amount of aqueous phase less than or equal to 30% of the total weight of the composition, it being possible for this amount to range, for example, from 10 to 30% by weight, and preferably from 15 to 30% by weight, relative to the total weight of the composition. The amount of water in the aqueous phase is not limited and can range, for example, from 5 to 30% by weight, and preferably from 10 to 25% by weight, relative to the total weight of the composition.

Conventionally, the aqueous phase can contain, besides the water, one or more water-soluble solvents chosen from polyols (or polyhydric alcohols), water-soluble lower alcohol(s), and mixtures thereof. The term "lower alcohol" is intended to mean an alcohol containing from 1 to 8 carbon atoms. As polyols, mention may, for example, be made of glycerol; glycols such as propylene glycol, butylene glycol or isoprene glycol and polyethylene glycols such as PEG-8; sorbitol; sugars such as glucose, fructose, maltose, lactose or sucrose; and mixtures thereof. As lower alcohols, mention may, for example, be made of ethanol, isopropanol, butanol and mixtures thereof. When they are present in the composition of the invention, the solvent(s) may be in an amount ranging from 0.01 to 60% by weight, preferably from 0.5 to 50% by weight, and better still from 5 to 20% by weight, relative to the total weight of the aqueous phase. These adjuvants and the concentrations thereof should be such that they do not modify the property desired for the composition of the invention.

Mineral and Organic Fillers

The composition according to the invention contains one or more mineral and/or organic fillers (solid particles) having an oil uptake greater than or equal to 75 ml/100 g.

The inventors have noted, surprisingly, that the addition of such fillers makes it possible to have a better oil release rate during massaging on the application support (e.g., skin, area around the eye, mucous membranes, scalp, eyelashes, hair).

The fillers used in the composition according to the invention are characterized by their oil uptake, i.e. their ability to adsorb castor oil. The oil uptake is determined by a method analogous to AFNOR standard NF T30-022, the linseed oil in this standard being replaced, here, with castor oil. The oil uptake corresponds to the amount of castor oil (in ml) required to obtain a firm and homogeneous paste with 100 g of fillers. The higher this value, the more the filler adsorbs the oil.

To determine the oil uptake according to the method used, analogous to AFNOR standard NF T30-022, an amount m (weight) of filler (1 to 20 grams) that is appropriate according to the probable oil uptake of the filler is used, as described in the AFNOR standard. This amount of filler is placed on a plate and castor oil is slowly added, at a rate of four to five drops at a time, by means of a pipette. After each addition, the oil is incorporated into the filler with a palette knife and the addition of the oil is continued at this rate until there is formation of conglomerations of oil and of filler. From then on, the oil is added dropwise and each addition is followed by vigorous trituration with the knife. The addition is stopped when a firm and smooth paste is obtained, that can be spread without cracks or the formation of lumps. The amount m2 of oil used in grams is then noted.

The oil uptake in ml/100 g corresponds to:

$$\frac{m_2 \times 100}{\rho_2 \times m}$$

$\rho_2$ being the density of castor oil=0.96 (reference for the density of castor oil: Manuel des corps gras [Manual of fatty substances] by J P Wolff, publisher Azoulay Paris, 1968, page 360).

Two measurements are carried out and the mean is taken.

The fillers that improve the oil release rate have an oil uptake greater than 75 ml/100 g, and preferably greater than or equal to 100 ml/100 g.

The addition of mineral and/or organic fillers having an oil uptake greater than or equal to 75 ml/100 g makes it possible to improve the amount of oil released, and in particular to improve the makeup-removing capacity of the composition when it is used for removing makeup from the skin or the eyelashes.

Not all mineral or organic fillers make it possible to release the oil rapidly. Thus, fillers such as the talc Luzenac 15 M00® (magnesium silicates) sold by the company Luzenac, or cornflour, Amidon De Mais B® sold by Roquette Frères, do not modify the oil release rate or can even slow it down, as is the case, for example, with 4% of talc, as shown in the comparative examples presented below. Thus, the mineral or organic fillers chosen according to the criteria described above make it possible to improve the oil release rate and to obtain a better effectiveness of fine O/W emulsions containing a large amount of oils.

The filler(s) used in the composition according to the invention may be mineral and organic, porous or nonporous, and spherical or nonspherical.

a—Mineral Fillers

Included as mineral fillers that can be used in the composition of the invention, mention may, for example, be made of silicon oxides such as silicas having a specific surface area greater than or equal to 120 m$^2$/g. The term "silica" is intended to mean both pure silicas, that may be hydrophilic or hydrophobic, and silica-coated particles. These silicas are preferably amorphous and they may be of fumed origin or of precipitated origin. They may be in pulverulent form or in the form of an aqueous dispersion. They are generally characterized by a specific surface area ranging from 120 to 800 m$^2$/g, a number-average elemental particle dimension ranging from 3 to 50 nm, a tapped density ranging from 40 to 200 g/l, and better still from 50 to 150 g/l, and an aggregate size ranging from 10 to 300 μm.

As silicas of this type, mention may, for example, be made of the silicas sold under the names Aerosil 150®, 200®, 300®, 380®, FK 320 DS®, R805®, R812® and R974® by the company Degussa-Hüls, and the silicas sold under the names Sunspheres H-31®, H-32®, H-33®, H-51®, H52®, H-121® or H-122®, having an oil uptake ranging from 150 to 400 ml/100 g and a specific surface area ranging from 700 to 800 m$^2$/g, by the company Dohkai Chemical Industries.

b—Organic Fillers

Included as organic fillers that can be used in the composition of the invention, mention may, for example, be made of microspheres of polyamide (Nylon) having a number-average size ranging from 5 μm to 30 μm, for instance those sold under the names Orgasol 2002 D NAT COS®, Orgasol 2002 UD NAT COS® or Orgasol 2002 EXD NAT COS® by the company Atofina, those sold under the names Micropan 777® and Microfine-Copolyamide 6/12® by the company Centerchem, and those sold under the name Ganzpearl GPA-700® by the company SPCI.

Mixtures of these organic and mineral fillers may be used.

The filler(s) is (are) preferably added to the composition after preparation of the emulsion.

The amount of fillers can range from 0.5 to 10% by weight, preferably from 0.5 to 5% by weight, relative to the total weight of the composition. The fillers/lipophilic constituents weight ratio preferably ranges from 0.006 to 0.08.

Additives

The composition according to the invention may also contain any adjuvant or additive, for example those conventionally used in the fields under consideration, and in particular in the cosmetics or dermatological fields.

Among the conventional adjuvants that may be contained in the aqueous phase and/or in the oily phase of the emulsions in accordance with the invention (according to the water-soluble or liposoluble nature of these adjuvants), mention may in particular be made of foaming surfactants that are anionic (such as sodium lauryl ether sulphate, sodium alkyl phosphate or sodium trideceth sulphate), amphoteric (such as alkyl betaine or disodium cocoamphodiacetate) or non-ionic with an HLB greater than 10 (such as POE/PPG/POE, alkylpolyglucoside, or polyglyceryl-3 hydroxylauryl ether); preserving agents; sequestering agents (EDTA); antioxidants; fragrances; dyestuffs such as soluble dyes, pigments and pearlescent agents; matifying, tensioning, bleaching or exfoliating fillers; sunscreens; cosmetic or dermatological active agents and agents having the effect of improving the cosmetic properties of the skin, that are hydrophilic or lipophilic; electrolytes. The amounts of these various adjuvants are those conventionally used in the field under consideration and are, for example, from 0.01 to 20% of the total weight of the composition.

As active agents that can be used in the composition of the invention, mention may, for example, be made of water-soluble or liposoluble vitamins such as vitamin A (retinol), vitamin E (tocopherol), vitamin C (ascorbic acid),vitamin B5 (panthenol) vitamin B3 (niacinamide), derivatives of these vitamins (in particular esters) and-mixtures thereof; antiseptics; antibacterial active agents such as 2,4,4'-trichloro -2'-hydroxy diphenyl ether (or triclosan) or 3,4,4'-trichlorocarbanilide (or triclocarban); antisebohrreic agents; antimicrobial agents such as benzyl peroxide, salicylic acid, triclosan, azelaic acid or niacin (vit. PP); slimming agents such as caffeine; optical brighteners, and any active agent that is suitable for the final purpose of the composition, and mixtures thereof.

The amount of active agents depends on the desired aim. The active agent(s) may, for example, be present at a concentration ranging from 0.001 to 20%, preferably from 0.01 to 10% by weight, and better still from 0.05 to 5%, of the total weight of the composition.

Of course, those skilled in the art will take care to choose the optional additive(s) of the composition according to the invention in such a way that the advantageous properties intrinsically associated with the composition in accordance with the invention are not, or are not substantially, altered by the envisaged addition.

The emulsions according to the invention can be obtained by means of a phase inversion process. This preparation process comprises:

1) Weighing out, into a container, all the constituents of the composition (with the exception of the thermosensitive starting materials and the fillers).
2) Homogenizing the mixture, for example by means of a Rayneri 350 rpm, and heating by gradually increasing the temperature, by means of a water bath, to a temperature greater than or equal to the phase inversion temperature T2, i.e. until a transparent or translucent phase (microemulsion or lamellar phase region) is obtained, followed by a more viscous white phase that indicates that the inverse emulsion (W/O) has been obtained.
3) Stopping the heating and maintaining the stirring until ambient temperature is again reached, passing through the phase inversion temperature T1, i.e. the temperature at which a fine O/W emulsion forms.
4) When the temperature has again dropped below the phase inversion temperature (T1) region, adding the fillers and, optionally, the thermosensitive starting materials.

A stable O/W emulsion is obtained in which the droplets of oil are fine.

While not bound by theory, it is believed that in the microemulsion formation region (translucent mixture), the hydrophilic and hydrophobic interactions are equilibrated since the tendency of the surfactant is to form both direct micelles and inverse micelles. By heating beyond this region, formation of a W/O emulsion (white opaque mixture) is obtained since the surfactant promotes the formation of a water-in-oil emulsion. Then, during the cooling below the phase inversion region, the emulsion becomes an O/W emulsion.

Phase inversion emulsification is explained in detail in the work T. Förster, W von Rybinski, A. Wadle, Influence of microemulsion phases on the preparation of fine disperse emulsions, Advances in Colloid and interface sciences, 58, 119-149, 1995, mentioned here by way of reference.

The compositions according to the invention are preferably in the form of more of less supple creams, and they can in particular constitute cosmetic or dermatological compositions, for example cosmetic compositions for the treatment of keratin materials such as the skin, the mucous membranes, the eyelashes, the hair and the nails. They can also constitute, for example, makeup-removing compositions and/or cleansing compositions and/or care compositions for the skin, the mucous membranes such as the lips, and/or for the eyelashes, compositions for massaging facial skin or body skin, scrubbing (or exfoliating) compositions both for the face and for the hands (when the composition contains exfoliating particles), antisun compositions (UV protection) and aftersun compositions. They may also constitute makeup compositions for keratin materials and in particular the skin, the lips and the eyelashes, and more particularly such as foundations, lipsticks or lip glosses after the addition of suitable pigments and/or fillers.

The compositions according to the invention can also be used as shower care balms (to be rinsed, for example by massaging in the product until the oil is released, and then rinsing the skin which is then soft and moisturized); as conditioners and hair care balms; as shaving products; as masks, including an aftersun repairing mask; as a slimming poultice on a region of "orange peel skin" (to be massaged in and then rinsed off); as a massage balm; as a lip repairing balm to be rinsed off; as a balm for dry feet. In these uses, the product is subsequently rinsed off.

When the composition is an exfoliating product (also called cleansing product), one preferably applies the product to the face or the hands or the body, with rubbing for one or two minutes, and then rinsing. The skin is then smooth, soft and cleansed.

A subject of the present invention is thus the cosmetic use of the composition as defined above, for the cosmetic treatment of keratin materials.

A subject of the present invention is thus also the cosmetic use of the composition as defined above, for removing makeup from and/or for cleansing the skin, the lips and/or the eyelashes.

A subject of the present invention is also the cosmetic use of the composition as defined above, for making up the skin, the lips and/or the eyelashes.

Another subject of the present invention is a cosmetic process for removing makeup from and/or cleansing the skin, including the scalp, the eyelashes, and/or the lips, wherein a composition as defined above is applied to the skin, the eyelashes and/or the lips.

The examples indicated below will make it possible to understand the invention more clearly without, however, being limiting in nature. The amounts indicated are in % by weight unless otherwise mentioned. The names are given as chemical names and as CTFA names according to the compounds. In some examples, the temperatures T1 and T2 corresponding to the temperatures bordering the phase inversion region are indicated.

The examples carried out were subjected to tests for measuring their advantages for removing makeup. These tests, that relate to the percentage of makeup removal and the oil release rate (or breaking rate), were carried out according to the following protocols:

I. In vivo Makeup-Removing Protocol
 I a. Material
1. Water-rinsable makeup-removing oil: "Huile Démaquillante fraîche" from Shu Uemura.
2. Household soap.
3. 1 masking card comprising an empty central portion cut out in a 4×4 cm Bristol board+1 Lumicolor permanent S marker pen.
4. CR300 calorimeter (L.a.b. colorimetry measurement)
5. Air Wear no-transfer foundation "Sable" LSF 12 from L'Oreal.
6. 8 small watch glasses+small spatulas.
7. 1 precision balance.
8. 1 stopwatch.
 I.b. Protocol
Four areas (2 per arm) having the size of the central portion cut out of the masking card are drawn on the skin using the marker pen and the masking card;
the skin in these areas is cleansed with the rinsable makeup-removing oil and then with soap, rinsed, and dried (the marks from the marker pen are therefore lightened so as to prevent any transfer of marker ink to the foundation at the time of application);
the naked skin is measured by colorimetry: 3 measurements of L, a, b per area (calorimeter reading head positioned right at the centre of the area);
16 mg+/−0.05 mg of foundation are applied evenly in the 4 delimited areas, and left for 30 minutes;
the skin with foundation is measured by colorimetry: 3 measurements of L, a, b per area;
208 mg+/−1 mg of makeup-removing composition to be tested are weighed out into the watch glasses 4 times;
the makeup is removed from each area with the finger by circular movement for 10 seconds and the area is then rinsed with tap water (warm; hardness not controlled), lightly brushing with the fingers of the available hand. This is done to the 4 areas without waiting;
the areas are dabbed with a Kleenex-type disposable handkerchief and left for 15 minutes (feeling that the skin is dry);
the skin from which the makeup has been removed is measured by colorimetry: 3 measurements of L, a, b per area.

The percentage makeup removal is calculated in the following way:
the colorimetric difference in the made-up skin (FdT skin) relative to the naked skin is determined, ΔEmax being the value corresponding to complete makeup removal:

$$\Delta E\max=\sqrt{(\Delta a_1^2+\Delta b_1^2+\Delta L_1^2)} \text{ with}$$

$\Delta a_1$=a naked skin−a FdT skin
$\Delta b_1$=b naked skin−b FdT skin
$\Delta L_1$=L naked skin−L FdT skin
For the makeup-removing composition tested, the colorimetric difference ΔE of the skin from which the makeup has been removed (remove skin) relative to the made-up skin (FdT skin) is determined for each area:

$$\Delta E=\sqrt{(\Delta a_2^2+\Delta b_2^2+\Delta L_2^2)} \text{ with}$$

$\Delta a_2$=a remove skin−a FdT skin
$\Delta b_2$=b remove skin−b FdT skin
$\Delta L_2$=L remove skin−L FdT skin
The ΔE/ΔEmax ratio is determined.
The mean makeup removal percentage, that is the mean of the 4 values of (ΔE/ΔEmax)×100, is calculated for the makeup-removing composition tested.

II. Measurement of the Oil Release Rate (Breaking Rate)
II.a. Material
1. Water-rinsable makeup-removing oil: "Huile Démaquillante fraîche" from Shu Uemura.
2. Household soap.

3. 1 masking card with a square central portion cut out in a 4×4 cm Bristol board+1 Lumicolor permanent S marker pen.
4. 4 small watch glasses+small spatulas.
5. 1 precision balance.
6. 1 stopwatch.

II.b. Protocol

Four areas (2 per arm) having the size of the central portion cut out in the masking card are drawn on the skin using the marker pen and the masking card;

the skin in these areas is cleansed with soap, rinsed, and dried (the marks from the marker pen are therefore lessened so as to prevent any transfer of marker ink into the foundation at the time of application);

an amount M of makeup-removing product is applied evenly in one of the delimited areas, M in mg being 100 mg+/−1 mg of makeup-removing product;

the stopwatch is started;

the area is massaged evenly, and the time taken for the oil to be released is noted, i.e. the moment when the product suddenly becomes more slippery under the fingers.

If t is the time, in seconds, taken for the oil to be released, the breaking rate (release of the oil) is equal to: t×100/M.

The test is repeated on the other three areas and the mean of the results is determined.

Alongside the examples according to the invention, comparative examples that do not satisfy the conditions of the compositions according to the invention were realized, and their viscosity at 25° C., their pH, the percentage makeup removal and the breaking rate were measured.

I. Examples With Silica (Example 1 According to the Invention) and Without Silica (Comparative Example 1)

| Composition | Example 1 according to the invention | Comparative Example 1 (no filler) |
|---|---|---|
| Eumulgin BA 10 ® (1) | 5 | 5 |
| Isopropyl palmitate ® (2) | 34.5 | 35 |
| 2-Ethylhexyl monococoate (3) | 34.5 | 35 |
| Propyl paraben | 0.15 | 0.15 |
| Methyl paraben | 0.15 | 0.15 |
| Glycerol | 10 | 10 |
| Deionized water | 14.45 | 14.45 |
| Chlorhexidine digluconate | 0.25 | 0.25 |
| Aerosil 200 ® (4) | 1 | — |
| Total | 100 | 100 |
| Total SA | 5 | 5 |
| Total oil | 70 | 70 |
| SA/oil ratio | 0.07 | 0.07 |
| T1 (° C.) | 69 | 73 |
| T2 (° C.) | 77 | 85 |
| Appearance | White, slightly translucent, supple cream | White, slightly translucent, supple cream |
| Viscosity (Pa · s) | 6.6 | 5 |
| pH | 5.9 | 5.8 |
| Oil release rate (s/100 mg) | 5 | 23 |
| % makeup removal | 96 | 90 |

(1) Eumulgin BA 10 ® sold by Cognis = oxyethylenated (10 EO) behenyl alcohol
(2) Isopropyl Palmitate ® sold by Cognis = isopropyl palmitate
(3) 2-ethylhexyl monococoate ® sold by Stéarineries Dubois
(4) Aerosil 200 ® sold by Degussa-Hüls = hydrophilic fumed silica (oil uptake: 460 ml/100 g; tapped density: 50 g/l; 200 m$^2$/g)

It emerges from this table that the addition of the silica used according to the invention clearly improves the oil release rate (also called "breaking rate") during application to the skin and the makeup-removing effectiveness of the composition of the invention.

II. Examples With Nylon Particles (Example 2 According to the Invention) and Without Nylon Particles (Comparative Example 2)

| Composition | Example 2 according to the invention | Comparative Example 2 (no filler) |
|---|---|---|
| Eumulgin BA 10 ® (1) | 5 | 5 |
| Ceraphyl 368 ® (5) | 65 | 68 |
| Propyl paraben | 0.15 | 0.15 |
| Methyl paraben | 0.15 | 0.15 |
| Glycerol | 10 | 10 |
| Deionized water | 13.45 | 14.45 |
| Ethanol | 2 | 2 |
| Chlorhexidine digluconate | 0.25 | 0.25 |
| Orgasol 2002 EXD NAT COS ® (6) | 4 | — |
| Total | 100 | 100 |
| Total SA | 5 | 5 |
| Total oil | 65 | 68 |
| SA/oil ratio | 0.08 | 0.07 |
| T1 (° C.) | 71 | 74 |
| T2 (° C.) | 82 | 82 |
| Appearance | White, slightly translucent, supple cream | White, slightly translucent, supple cream |
| Viscosity (Pa · s) | 6.6 | 5 |
| pH | 5.9 | 5.8 |
| % makeup removal | 97 | 93 |
| Oil release rate (s/100 mg) | 22 | 36 |

(1) Eumulgin BA 10 ® sold by Cognis = oxyethylenated (10 EO) behenyl alcohol
(5) Ethylhexyl palmitate; Ceraphyl 368 ® sold by ISP or Cegesoft C24 ® sold by Cognis
(6) Nylon-12; Orgasol 2002 EXD NAT COS ® sold by Atochem (oil uptake: 100 ml/100 g; specific surface area: 4 m$^2$/g; 10 μ; density: 1.02)

It emerges from this table that the addition of the Nylon particles used according to the invention clearly improves the oil release rate (or breaking rate) during application to the skin and the makeup-removing effectiveness of the composition of the invention.

III. Comparative Examples 3 to 5

Examples Containing Fillers that do not have an Oil Uptake Greater than or Equal to 75 ml/100 g

| Composition | Comparative Example 3 with 1% of talc | Comparative Example 4 with 4% of talc | Comparative Example 5 with 4% of starch |
|---|---|---|---|
| Eumulgin BA 10 ® (1) | 5 | 5 | 5 |
| Ceraphyl 368 ® (5) | 68 | 68 | 68 |
| Propyl paraben | 0.15 | 0.15 | 0.15 |
| Methyl paraben | 0.15 | 0.15 | 0.15 |
| Glycerol | 10 | 10 | 10 |
| Deionized water | 13.45 | 13.45 | 13.45 |
| Ethanol | 2 | 2 | 2 |
| Chlorhexidine digluconate | 0.25 | 0.25 | 0.25 |
| Luzenac 15 M 00 ® (7) | 1 | 4 | — |
| Amidon De Mais B ® (8) | — | — | 4 |
| Total | 100 | 100 | 100 |
| Total SA | 5 | 5 | 5 |
| Total oil | 68 | 68 | 68 |

| Composition | Comparative Example 3 with 1% of talc | Comparative Example 4 with 4% of talc | Comparative Example 5 with 4% of starch |
|---|---|---|---|
| SA/oil ratio | 0.07 | 0.07 | 0.07 |
| T1 (° C.) | 71 | 71 | 71 |
| T2 (° C.) | 82 | 82 | 82 |
| Appearance | White, slightly translucent, supple cream | White, slightly translucent, supple cream | White, slightly translucent, supple cream |
| Viscosity (Pa · s) | 6.9 | 5.4 | 7.8 |
| pH | 5.8 | 5.8 | 5.8 |
| Oil release rate (s/100 mg) | 35 | 49 | 36 |

(1) Eumulgin BA 10 ® sold by Cognis = oxyethylenated (10 EO) behenyl alcohol
(5) Ethylhexyl palmitate; Ceraphyl 368 ® sold by ISP
(7) Talc: magnesium silicate (CI: 77718) sold by the company Luzenac (oil uptake: 45 ml/100 g; particle size: 5 µm; specific density: 2.8; tapped density: 0.63 g/cm³; specific surface area: 4.6 m²/100 g)
(8) *Zea Mays* (Corn) Starch by the company Roquette Frères (oil uptake: 58 ml/100 g)

This table shows that the particles that do not have the claimed characteristics do not make it possible to obtain an improved oil release rate with respect to Comparative Example 2 (that does not contain particles).

IV. Examples 3 to 6 According to the Invention

| Starting material | Example 3 according to the invention | Example 4 according to the invention | Example 5 according to the invention | Example 6 according to the invention |
|---|---|---|---|---|
| Eumulgin BA 10 ® (1) | 5 | 5 | 5 | 5 |
| Isocetyl stearate (9) | — | — | 23.3 | — |
| Cetiol OE ® (10) | — | — | 43.7 | — |
| Mineral oil (11) | 68 | — | — | 65 |
| Apricot oil (12) | — | 68 | 3 | — |
| Liquid fraction of shea butter | — | — | — | 3 |
| Propyl paraben | 0.15 | 0.15 | 0.15 | 0.15 |
| Methyl paraben | 0.15 | 0.15 | 0.15 | 0.15 |
| Glycerol | 10 | 10 | 10 | 10 |
| Deionized water | qs 100 | qs 100 | qs 100 | qs 100 |
| Ethanol | 2 | 2 | 2 | 2 |
| Chlorhexidine digluconate | 0.25 | 0.25 | 0.25 | 0.25 |
| Aerosil 200 ® (4) | 1 | — | 1 | 1 |
| Orgasol 2002 EXD NAT COS ® (6) | — | 4 | — | — |
| Total | 100 | 100 | 100 | 100 |
| Total SA | 5 | 5 | 5 | 5 |
| Total oil | 68 | 68 | 70 | 68 |
| SA/oil ratio | 0.07 | 0.07 | 0.07 | 0.07 |
| Appearance | White supple cream | Cream-coloured supple cream | Cream-coloured supple cream | Cream-coloured supple cream |
| Viscosity (Pa · s) | 5.5 | 5 | 6.6 | 5 |
| pH | 5.8 | 5.8 | 5.8 | 5.8 |
| Use | Massage cream for the body | Massage cream for the body or the face | Massage cream for the face | Cream for around the eyes |

(1) Eumulgin BA 10 ® sold by Cognis = oxyethylenated (10 EO) behenyl alcohol
(4) Aerosil 200 ® sold by Degussa-Hüls = hydrophilic fumed silica (oil uptake: 460 ml/100 g; tapped density: 50 g/l; 200 m²/g)
(6) Nylon-12; Orgasol 2002 EXD NAT COS ® sold by Atochem (oil uptake: 100 ml/100 g; specific surface area: 4 m²/g; 10 µ; density: 1.02)
(9) Isocetyl stearate = Isocetyl Stearate ® sold by Stéarineries Dubois
(10) Dicaprylyl ether = Cetiol OE ® sold by Cognis
(11) Mineral oil = Marcol 82 ® sold by Esso
(12) Apricot oil = Apricot Kernel Oil ® sold by Desert Whale

V. Examples 7 and 8 According to the Invention

| Starting material | Exfoliant massage cream for the body or the face | Conditioner balm |
|---|---|---|
| Eumulgin BA 10 ® (1) | 5 | 5 |
| Mineral oil (11) | — | 68 |
| Ceraphyl 368 (5) | 68 | — |
| Polyquaternium-7 (13) | — | 0.5 |
| Propyl paraben | 0.15 | 0.15 |
| Methyl paraben | 0.15 | 0.15 |
| Glycerol | 10 | 10 |
| Ethanol | 2 | 2 |
| Chlorhexidine digluconate | 0.25 | 0.25 |
| Aerosil 200 ® (4) | 1 | 1 |
| Gotalene 120 Incolore 2 ® from Dupont (14) | 4 | — |
| Deionized water | qs 100 | qs 100 |
| Total | 100 | 100 |
| Total SA | 5 | 5 |
| Total oil | 68 | 68 |
| SA/oil ratio | 0.07 | 0.07 |
| Appearance | White supple cream | Cream-coloured supple cream |
| Viscosity (Pa · s) | 5.5 | 5 |
| pH | 5.8 | 5.8 |

(1) Eumulgin BA 10 ® sold by Cognis = oxyethylenated (10 EO) behenyl alcohol
(4) Aerosil 200 ® sold by Degussa-Hüls = hydrophilic fumed silica
(5) Ethylhexyl palmitate; Ceraphyl 368 ® sold by ISP
(13) Polyquaternium-7 = Merquat S ® sold by Ondeo Nalco
(14) Gotalene 120 incolore 2 ® sold by Dupont = polyethylene powder The above written description of the invention provides a manner and process of making and using it such that any person skilled in this art is enabled to make and use the same, this enablement being provided in particular for the subject matter of the appended claims, which make up a part of the original description and including a composition for topical application in the form of an oil-in-water emulsion, wherein it contains:

a lipophilic phase (A) present in an amount of at least 60% by weight relative to the total weight of the composition, an aqueous phase (C) present in an amount of less than or equal to 30% by weight relative to the total weight of the composition, an emulsifying system (B) present in an amount of 2 to 20% by weight relative to the total weight of the composition and comprising at least one emulsifier having an HLB ranging from 8 to 18, from 0.5 to 10% by weight, relative to the total weight of the composition, of one or more fillers having an oil uptake greater than or equal to 75 ml/100 g, the emulsifying system (B)/lipophilic phase (A) ratio ranging from 0.04 to 0.2.

Also fully described and enabled is a process for preparing a composition according to the invention, comprising:

1) weighing out, into a container, all the constituents of the composition (with the exception of the thermosensitive starting materials and fillers).

2) Homogenizing the mixture, and heating by gradually increasing the temperature, by means of a water bath, to a temperature greater than or equal to the phase inversion temperature T2.
3) Stopping the heating and maintaining the stirring until ambient temperature is again reached, passing through the phase inversion temperature T1.
4) When the temperature has again dropped below the phase inversion temperature (T1) region, adding the fillers and, optionally, the thermosensitive starting materials.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out. Terms such as "contain(s)" and the like as used herein are open terms meaning 'including at least' unless otherwise specifically noted.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A composition in the form of an oil-in-water emulsion, comprising:
    a lipophilic phase (A) in an amount of at least 60% by weight relative to the total weight of the composition;
    an emulsifying system (B) in an amount of 3 to 11% by weight relative to the total weight of the composition;
    an aqueous phase (C) in an amount of less than or equal to 30% by weight relative to the total weight of the composition; and
    at least one filler in an amount of from 0.5 to 5% by weight relative to the total weight of the composition;
    wherein:
    the emulsifying system comprises at least one emulsifier having an HLB ranging from 10 to 16 wherein said emulsifier is an addition product of ethylene oxide with behenyl alcohol;
    the filler has an oil uptake greater than or equal to 75 ml/100 g;
    the filler comprises at least one of a silica having a specific surface area greater than or equal to 120 m$^2$/g and polyamide microspheres having a number-average size ranging from 5 μm to 30 μm; and
    a weight ratio of the emulsifying system (B) to the lipophilic phase (A) is from 0.04 to 0.2, and
    the lipophilic phase (A) comprises at least one fatty ester, wherein the fatty ester of the lipophilic phase is obtained from an alcohol comprising a linear or branched chain, having from 1 to 17 carbon atoms, and from a fatty acid comprising a linear or branched chain, having from 3 to 18 carbon atoms.

2. The composition according to claim 1, wherein the composition is obtained by phase inversion emulsification.

3. The composition according to claim 1, wherein a mean size of droplets of oily phase D[4.3] ranges from 0.09 μm to 4 μm.

4. The composition according to claim 1, having a viscosity at 25° C. of greater than or equal to 1 Pa·s.

5. The composition according to claim 1, wherein the composition further comprises an emulsifier selected from the group consisting of ethoxylated fatty alcohols, ethoxylated fatty acids, partial glycerides of ethoxylated fatty acids, polyglycerolated fatty acid triglycerides and their ethoxylated derivatives, and mixtures thereof.

6. The composition according to claim 5, wherein the composition further comprises an emulsifier selected from the group consisting of addition products of ethylene oxide with lauryl alcohol; addition products of ethylene oxide with cetearyl alcohol; addition products of ethylene oxide with cetyl alcohol; addition products of ethylene oxide with stearyl alcohol; addition products of ethylene oxide with isostearyl alcohol; addition products of ethylene oxide with lauric acid, palmitic acid, stearic acid or behenic acid, and mixtures thereof.

7. The composition according to claim 1, comprising beheneth-10.

8. The composition according to claim 1, wherein the emulsifying system further comprises one or more coemulsifier(s) chosen from fatty alcohols having 8 to 30 carbon atoms; fatty acids having 8 to 30 carbon atoms; fatty esters of glycerol; oxyethylenated derivatives thereof containing 2 to 8 ethylene oxide groups, and mixtures thereof.

9. The composition according to claim 1, wherein the amount of emulsifying system ranges from 3 to 16% by weight relative to the total weight of the composition.

10. The composition according to claim 1, wherein the amount of lipophilic phase ranges from 60 to 80% by weight relative to the total weight of the composition.

11. The composition according to claim 1, wherein the amount of fillers is 0.5 to 5% by weight relative to the total weight of the composition.

12. The composition according to claim 1, wherein the composition is a cosmetic or dermatological composition.

13. The composition according to claim 1, wherein the composition is a makeup-removing composition and/or a cleansing composition for the skin, the lips and/or the eyelashes, a composition for massaging facial skin and/or body skin, an exfoliating composition, an antisun composition or an aftersun composition, a shower care balm, a conditioner composition, a hair care balm, a shaving product, a mask, a slimming poultice, a massage balm, a lip repairing balm, or a balm for dry feet.

14. The composition according to claim 1, wherein said emulsifier comprises from 9 to 50 oxyethylenated groups.

15. The composition according to claim 1, wherein the emulsifying system (B) is present in an amount of 3 to 11% by weight relative to the total weight of the composition.

16. A process, comprising applying the composition according to claim 1 to a keratin material.

17. The process according to claim 16, wherein said composition is applied to skin, the lips and/or the eyelashes.

18. The process according to claim 16, wherein said composition is applied for removing makeup from and/or for cleansing the skin, the lips and/or the eyelashes.

19. The process according to claim 16, wherein said composition is applied for making up the skin, the lips and/or the eyelashes.

20. A process for preparing the composition according to claim 1, comprising:

1) homogenizing a mixture of the components of said lipophilic phase (A), said emulsifying system (B), and said aqueous phase (C) with the exception of any thermosensitive starting materials and heating by gradually increasing the temperature to a temperature greater than or equal to the phase inversion temperature T2,
2) stopping the heating and stirring until ambient temperature is reached, the mixture passing through phase inversion temperature T1,
3) after the temperature has dropped below the phase inversion temperature (T1) region, optionally adding any thermosensitive starting materials.

* * * * *